United States Patent [19]

Evans

[11] Patent Number: 5,642,936
[45] Date of Patent: Jul. 1, 1997

[54] METHODS FOR IDENTIFYING HUMAN HEREDITARY DISEASE PATTERNS

[75] Inventor: Steven Evans, Omaha, Nebr.

[73] Assignee: OncorMed, Gaithersburg, Md.

[21] Appl. No.: 593,446

[22] Filed: Jan. 29, 1996

[51] Int. Cl.$^6$ .................................................. A61B 5/00
[52] U.S. Cl. ........................................ 128/630; 128/924
[58] Field of Search ................ 364/413.01, 413.02; 128/630, 897, 898, 906

[56] References Cited

U.S. PATENT DOCUMENTS 4,197,854  4/1980  Kasa ..................................... 364/413.03
5,463,548  10/1995  Asada et al. .......................... 364/413.02

OTHER PUBLICATIONS

Medinfo '95, Proceedings of the Eighth World Congress on Medical Informatics, Vancouver, British Columbia, Canada, Jul., 1995 (Tsumoto et al., pp. 861–865).

Journal of the American Medical Informatics Association, Proceedings of the Nineteenth Annual Symposium on Computer Applications in Medical Care, New Orleans, Louisiana, Oct., 1995 (Tsumoto et al., pp. 270–274).

*Primary Examiner*—William E. Kamm
*Assistant Examiner*—George R. Evanisko
*Attorney, Agent, or Firm*—Rothwell, Figg, Ernst & Kurz

[57] ABSTRACT

The present invention relates to a method of determining human hereditary disease risk factors, a method of determining hereditary cancer patterns presenting in cancer family histories, and a method of determining whether a cancer family history represents a hereditary pattern.

5 Claims, 5 Drawing Sheets

Step 1:

> Collect database of records for persons $p_j$

Step 2:

> Expand database of records yielding $P_j$

Step 3:

> Select index cancer(s) of interest for $P_j$

Step 4:

> For each record in $P_j$ with index cancer, calculate values for each $f_i$

> Assign $v_j$ to each record where $v_j = \sum \alpha_i f_i$

> Assign T(true) to each record in $P_j$ if $v_j \geq V_i$; otherwise F(false)

> $V_j$: As output, have a labeled database $V_j$ of all records in $P_j$ with label T or F

FIG. 1A  (A)

Step 1: Cancer record of pi

| Person $p_i$ | Cancer(s) of $p_i$ | Mother of $p_i$ | Father of $p_i$ | Daughter of $p_i$ |
|---|---|---|---|---|
| Sally | breast at 44 | breast at 48 | --- | --- |

Step 2: Expand database into pattern ser Pi

| Person $p_i$ | Cancer(s) of $p_i$ | Mother of $p_i$ | Father of $p_i$ | Daughter of $p_i$ |
|---|---|---|---|---|
| Sally | breast at 48 | --- | --- | breast at 44 |

Step 3: Select index cancer

For example, focus on breast cancer

Step 4: Calculate values for each $f_i$

Let $f_1$ = #cancer(s) in the same generation
$f_2$ = # cancer(s) between generations
$f_3$ = # relatives with any type of cancers
$f_4$ = # relatives with same kind of cancer
$f_5$ = # cancer(s) at an early age of onset Assign weights for each $f_i$ to modulate $f_i$ and assign $v = \sum \alpha_i f_i$ to each record in $P_i$ Assign T to record if $v_i$ for record exceeds a threshold value $V_i$ selected for index cancer The database $V_i$ now has labeled "true" (else false) examples for the picked index cancer

FIG. 1A1

Step 5:

A labeled database of true and false cases is standard input into data mining software Data mining software permits user to select any variables in each record as the elements of interest from which the software creates a rule set using those variables. In our method, we first select genetic principles $f_i$, then any cancer occurrences $ca_i$.

Rule sets are created in which $f_i$ and then $ca_i$ are used to develop patterns which define set membership for the designated T records A significant rule is one for which the data mining software indicates that 5% or more of the $T_{(true)}$ cases in $P_i$ are examples of this rule The specific $f_i$'s and $ca_i$'s in the significant rule sets are the significant variables we will use to characterize the set of $T_{(true)}$ cases in $P_i$ Step 6:

Data mining software creates a rule-based system of combined $f_i$'s and $ca_i$'s which define set membership of the $T_{(true)}$ cases in $P_i$ Stand-alone rule set created Significant rules calculated as in Step 5

Herediatary Cancer Recognizer R created, comprised of set of patterns defined by genetic princiles $f_i$ and cancers $ca_i$

METHODS FOR IDENTIFYING HUMAN HEREDITARY DISEASE PATTERNS

BACKGROUND OF THE INVENTION

The present invention relates to a method of determining human hereditary disease risk factors, a method of determining hereditary cancer patterns presenting in cancer family histories, and a method of determining whether a cancer family history represents a hereditary pattern.

Recognition of the role of heredity in cancer has increased steadily over time and is discussed in Lynch et al. *Genetic Epidemiology of Cancer*, Boca Raton: CRC Press, (1989). For example, Lynch et al., *Surg. Clin. Of NA*, 70:753-774, (1990) has estimated that approximately 9% of carcinoma of the breast is consistent with hereditary breast cancer, and an additional 15–20% will be clearly familial. In addition, the potential for gene testing to confirm hereditary cancer has escalated in recent years, with the discovery of genes that cause breast cancer, colon cancer, and several other cancer syndromes. However mass testing of the population with dozens of expensive gene tests is not viable. The most effective way to identify hereditary cancer families has been with a detailed and accurate cancer family tree. It has been noted, that "[a] thoroughly compiled family history of cancer harbors the potential of being the most cost beneficial component of the patient's workup" (Lynch, H T, "Cancer and the family history trail, *New York State Journal of Medicine*, pp. 145-147, April, 1991). From such a family tree, the patterns of hereditary cancer can be detected by expert clinical oncologists. Subsequently proper surveillance and management may then be ascertained in concert with judicious gene testing, if and when available, to confirm the risk evaluation.

Unfortunately physicians generally do not take a detailed cancer family history. One study found that in most cases, "the family history of cancer had either been omitted altogether or reported as negative, despite substantial evidence to the contrary" (Lynch, H T et al. Family history in an oncology clinic: Implications for cancer genetics," *J. AMA;* 242:1268-1272, 1979.). Documentation of the failure to apply proper genetic principles or to obtain necessary family cancer histories has been repeatedly obtained.

Hereditary cancer pattern recognition has been difficult, given that: 1) there are now over 200 types of hereditary cancer syndromes, 2) the family history relayed from the patient can be "fuzzy" and imprecise, and 3) the variation among all the patterns may have billions of different presentations.

In the development of expert systems to mimic clinical experts, experts are studied, and guesses or observations are made as to what rules they are applying for specific cases. This process of study may or may not find or recognize rules, is dependent upon the reporting of the expert, and does not automatically create any rule set, but is dependent upon the insights of an observer. It is observer-dependent, not data-dependent. In addition, such construction and validation can require very long periods of time. Since the hereditary cancer field is constantly changing with new patterns uncovered, an expert system may be obsolete by the time it is developed. In addition, usually any one expert does not have the expertise to cover all the known hereditary cancer syndromes, but combining a version of one rule set from one expert with another rule set from another expert may yield inconsistent results. Finally and perhaps most important, any one expert's rule set is just that: the opinion of one expert. There are different philosophies in medicine as to what issues should be factored in, leading to dissension and confusion.

SUMMARY OF THE INVENTION

The present invention relates to a method of determining human hereditary disease risk factors, a method of determining hereditary cancer patterns presenting in cancer family histories, and a method of determining whether a cancer family history represents a hereditary pattern implemented on a computer.

More specifically, the invention relates to a method for determining the existence of a hereditary disease risk in a patient, comprising the steps of: compiling in a computer a database made up of a plurality of records each pertaining to an individual and containing a history of at least one specific disease in a family of that individual, with a plurality of parameters relating to each family member identified in the history; defining a plurality of functions each pertaining to one of the parameters and assigning predetermined weights to the functions based on values of the parameters; for each record in the database, summing the weights obtained for each of the functions to obtain a total value for each of the functions, identifying the record as presenting a hereditary pattern if the total value is above a predetermined threshold, and grouping the identified record into a subset of records; for each record in the database, applying expert knowledge generated rules to independently identify records as presenting hereditary patterns; comparing the independently identified records with the subset of records, and validating defined functions if a predetermined minimum percentage of records in the subset are consistent with the independently identified records; and using validated functions as a recognizer of hereditary disease patterns in a family history of the patient.

The invention also relates to a method wherein the plurality of records contain histories of instances of cancer including breast, ovarian, endometrial, prostate, malignant melanoma and colon cancer.

The present invention further relates to a method including the step of assigning weights to particular attributes used in the functions, and defining attributes as significant in the definition of specific hereditary disease patterns if a minimum percentage of records in the subset are consistent with the independently identified records.

This invention also relates to a method wherein an additional record is created in the database for each relative of the individual who is identified as having had the disease.

BRIEF DESCRIPTION OF THE DRAWINGS

FIGS. 1A–1C is a flow chart diagram indicating the steps in one embodiment of the invention.

DETAILED DESCRIPTION OF THE INVENTION

Figure 1B:
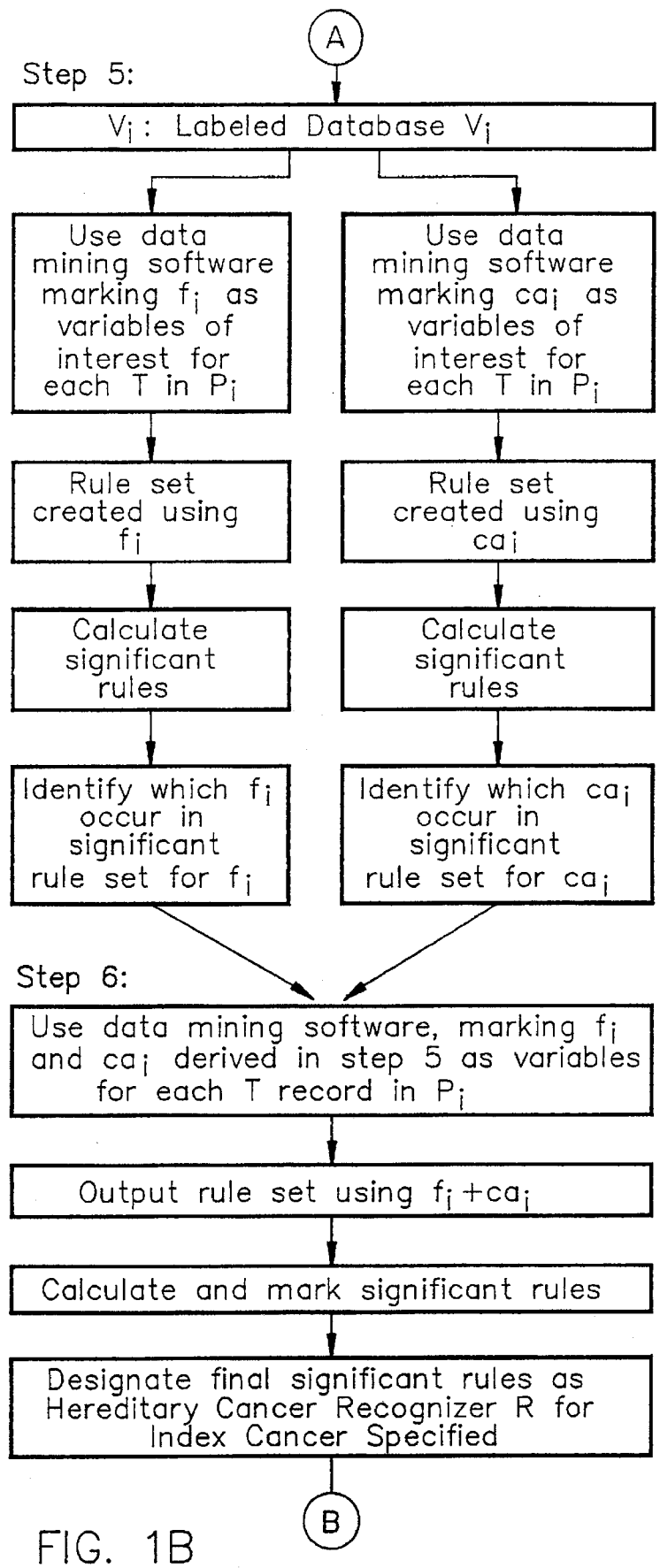
Figure 1C:
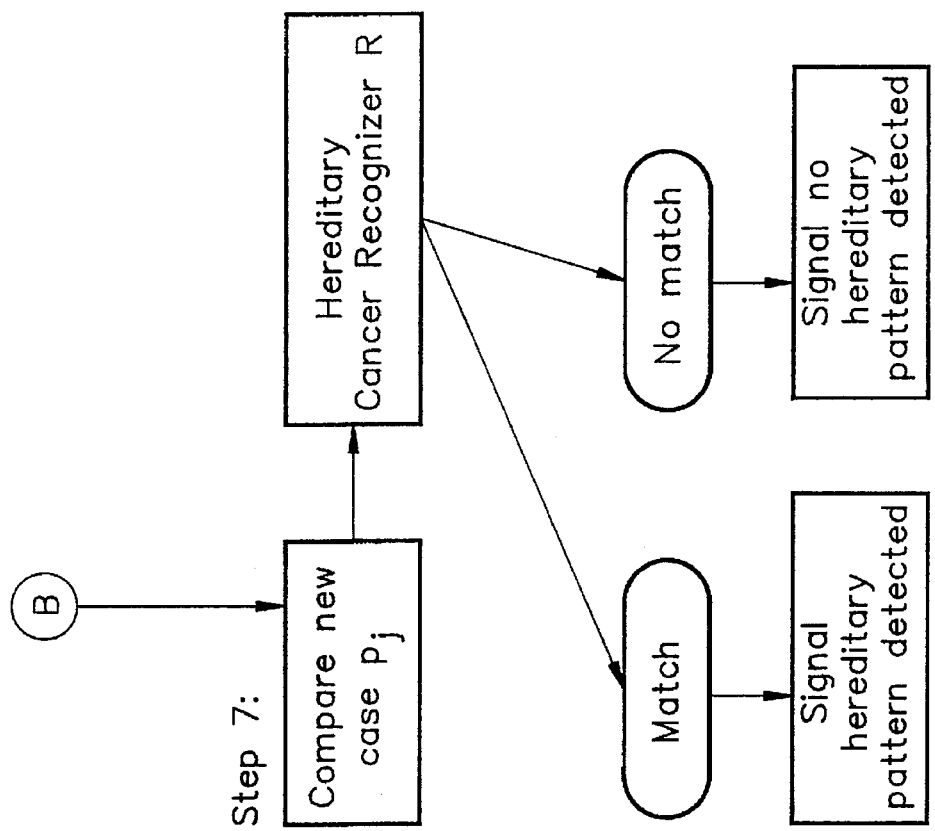

In order to provide an understanding of several of the terms used in the specification and claims, the following definitions and explanations are provided: Data Mining: As used herein, the term data mining is intended to mean a procedure that takes given examples of a specific condition and calculates rules that define set membership. For example, if individual history patterns were already classified as to whether they are hereditary or not, data mining would select factors within each pattern which imply the hereditary condition. In Table 1, the following condition are used as an example:

TABLE 1

| Patient List | F1 = Mother had cancer | F2 = Father had cancer | F3 = Mother's sister had cancer | F4 = Father's brother had cancer | Is this case an example of a hereditary cancer patient? |
|---|---|---|---|---|---|
| John | yes | yes | no | no | no |
| Sally | yes | no | yes | no | yes |
| Fred | no | yes | yes | no | no |
| Joe | yes | no | no | yes | no |
| Ann | no | yes | no | yes | yes |

Then any data mining procedure would be able to find the two rules:

```
If                F1 and F3
-or-
If                F2 and F4
THEN (mmeting either rule) implies a
"hereditary cancer pattern"
```

One uses the pathway-searching power of a comparison (data mining) algorithm to find predictive patterns. Note that in the instant invention, there is no indication which, if any, are the "example cases" of hereditary cancer in the data in order that one might obtain a logical rule set from data mining methods.

Expert Rule: The term expert rule is intended to mean a set of rules, each of which is comprised of logical measurable conditions, in mathematics, called a testable predicate which is an expression or condition that can be determined to be true or false based on measurement or data, wherein these conditions are joined by logical operators, including the operators AND, OR, and NOT, having the usual logical meaning. Given an example of the pattern about which the rule is concerned, one can examine the measurable characteristics of a pattern and ascertain whether it satisfies all the conditions of one or more of the rules in an expert rule set.

Recognizer: The term recognizer is intended to mean a rule set for a class of patterns for which any member of the class satisfies one or more of the rules in the rule set. For example, a set of reasonable conditions might be:

a) for a specific person "p", there was a colon cancer in a first-degree relative of that person, b) for a specific person "p", there was a colon cancer occurring before age 35 in a first-degree family member relative c) for a specific person "p", there were three or more cases of colon cancer in first or second-degree relatives And one rule might be: (a) AND ((b) OR (c))

The meaning of this rule is that if a person had a first-degree relative with colon cancer and that person had either a first degree relative with colon cancer occurring before the age of 35 or had three or more cases of colon cancer in first or second degree relatives, then that person's pattern meets or satisfies the rule. If this is one of the rules for a recognizer of hereditary colon cancer, then the person's pattern is said to be classified as a member of the recognized pattern set i.e., the pattern is a hereditary colon cancer pattern. If any member of the class of patterns constituting hereditary colon cancer were to fit the rule above, the rule above would then be the rule set or recognizer of hereditary cancer, although obviously the set usually has many different rules in order to successfully classify all possible presentations of the pattern. The actual recognizer for hereditary colon cancer has approximately 15 complex rules, each with several composite conditions or elements.

Neural Nets: The term neural nets is intended to mean mathematical algorithms which can assign weights to attributes which describe a situation so that a presentation of attributes can be tested to see if it qualifies as an example of the thing being recognized. Like data mining, development of neural nets assumes there is an assignment to the individual descriptions in the database indicating whether an entry is a member of the set of things being recognized or not. In the simplest form, for a case presented to a neural net, the outcome of a neural net is a value, which if greater than a certain amount, signifies the case is confirmed as true. The net does not however provide a rule or disclose what the logical relationship is among the attributes which led to the assignment of "true." Hence the net provides no explicit clinical evaluation, but is essentially like litmus paper which signals a positive or negative result. In Table 1, a neural net approach could yield the equation IF $a(F1 + F3) + b(F2 + F4) \geq 4$ THEN "signal (possible) hereditary cancer pattern"

where $a=2$, $b=2$, each $F$ is 1 or 0 depending on whether it is true or false.

The method of the present invention uses a computer database of cancer family histories, and from such information, automatically creates "IF-THEN" rule-based expert systems capable of determining or testing whether a cancer family history represents a hereditary cancer pattern. The term "recognizer" is used to signify the end result of the method's implementation. Unlike neural network software applications or data mining software applications, the present invention does not presume any definition or marker in the data indicating whether any cancer family history represents an example of a hereditary cancer family.

The instant invention creates a pool of likely hereditary cancer candidates among the cancer family history cases in the database and then extrapolates from these cases the nature of hereditary cancer patterns. Core genetics principles are employed which tend to characterize cases that would be good candidates for representing hereditary cancer. For example, one such principle is that typically hereditary cancer arises much earlier in the patient's life than does non-hereditary cancers. The application of a set of key principles will divide the set of all cases into those which reflect some mix of these principles, beyond a threshold, and those that do not. The degree to which the principles apply in a case is the extent to which a case tends to be a candidate to represent a hereditary pattern. All such cases that exceed some measurable threshold will be declared confirmed candidates for representing a possible hereditary pattern.

A second stage of the present invention is to take the cases that are confirmed candidates and then determine both the genetic principles which classify the confirmed candidates as well as the patterns of cancers in these cases which characterize the candidates. Specifically two sets of rules are determined which classify the cases into various composite pattern sets wherein each rule describes one or more patterns. This stage uses software called data mining techniques in order to obtain computer-generated rules which group or classify the candidate cases, using first the genetic principles and then the cancer family history patterns. In the first instance, the genetic principles characterize the candidate cases by a rule set in which the use of a genetic principle in the set indicates that this principle is a factor in the overall determination of hereditary cancer for the index cancer designated. These second rule set is a refining definition based on cancer patterns for the candidate cases. Each rule in the second set is examined, and the specific cancers used in each rule become the cancers which characterize the index cancer, e.g., endometrial cancer is a coincident cancer in rules that characterize colon cancer.

In the third stage, these coincident cancers are combined with the candidate-defining genetic principles to create the complete recognizer which is a composite set of clinically oriented defining rules.

One method of the present invention includes the following steps:

Step 1. The first step is to obtain a database which contains the cancer family history of cancer-affected individuals. There is nothing special about the form of the data, except that the data must contain the cancer family history of individuals. The essence of the information needed for each person (called a "proband") in the initial database is the following information concerning the cancer family history:

a) All first and second degree relatives of the proband are labeled, and each person is identified who has had cancer along with how he or she relates to the proband (such as, "it is the proband's mother's sister").

b) Enumeration of the types of cancer each blood relative of the proband has had, and the age of the person when he or she was diagnosed.

Step 2. Second, for every individual in the proband's cancer history who has had cancer, another cancer record is created describing the whole cancer family history relative to that person. For example, if a woman as proband had breast cancer and her mother did also, in addition to this master record, a second new record would be added for the mother as proband, indicating she had a daughter who had breast cancer. All such new records are added for both the maternal and the paternal side. Thus every entry represents some cancer-affected person indexed by a specific cancer. If a person's family history indicates more than one cancer, the family history permits the definition of multiple entries with one entry for each cancer type exhibited. What this first key step does is multiply the individual case histories of patients, with all the variations that can occur, into a richer universe of patterns. This transposition of patterns from all points of the family view multiples the universe of pattern considerations into a set many times greater than the first, significantly expanding the ultimate fidelity of the recognizer created. It also expands the variations on how cancer patterns may be viewed and considered.

Step 3. Once the individual cancer family histories are expanded into many different cancer family patterns, a specific cancer or cancers, of interest to be recognized is specified, e.g., breast cancer, and all entries in the newly expanded database of patterns which are indexed by the selected cancer are retrieved. Although several cancers may be picked at once with multiple cancers being an additive case, we shall give this description as if only one index case was selected, merely for ease of explanation.

Step 4. Next, a further subset of all the cancer histories concerned with the cancer of interest is selected which shall represent candidate hereditary cancer cases from which common patterns are extrapolated. This is accomplished by positing a set of descriptors or genetic principles which typically are known to be involved in hereditary disease. One such descriptor is "early-age-of-onset," since hereditary cancers tend to occur earlier than normal. Each descriptor is quantified. For example, if a cancer family history has a cancer occurring before the age of 50, one point is assigned; if there is a cancer occurring below the age of 45, two points are assigned; and if one occurs before the age of 35, three points are assigned. In the instant invention five such descriptors have been employed although the method in general could be instantiated with as many principles as desired. These genetic principles can include (1) early age of onset, (2) presence of cancer over several generations, (3) several cancers in the same generation, (4) multiple cases of the same cancer occurring, and (5) a high proportion of the relatives in the family expressing cancer. Each is quantified assigning increasing points the more the principle is expressed in the case history. Cases with a certain total score or higher are then labeled as candidates for the group that represents a hereditary cancer pattern and are then selected for further analysis. Although the principles have been quantified, the actual point assignments can be changed without changing the essential process. In addition, other principles can be added without changing the essential process.

Step 5. The subset of candidates from step 4 is labeled "true" for the purposes of now running off-the-shelf data mining software, such as Datalogic/R1.3 from Reduct Systems, Inc., which hypothesizes IF-THEN rules to describe how attributes of the marked "true" cases can characterize the "true" set. Each member of the "true" set has two different sets of defining attributes.

a) Genetic principles with individual point totals indicating how each principle contributed to the overall score, as well as a total score above a threshold value, and b) The occurrence of different cancers in the family for each case of the "true" set.

The data mining software is used first with one set of attributes, the genetic principles, and then with the other, the occurrences of cancer. The outcome of such a procedure is a set of rules using the attributes (genetic principles in the first case, cancer pattern types in the second) in which these attributes characterize the "true" set as much as possible. For example, a rule using the genetic attributes might be "IF a case accrues at least 6 points on early-age-of-onset plus at least 3 points for "multi-generational cancers", then 100% of the time such a case is one of the "true" cases," as "true" is defined by being a candidate as derived in step 4. Similarly, a rule for the cancer patterns might be, "if there are at least 2 first-degree family breast cancers, such as in your mother or sister, and at least 2 second-degree breast cancers such as in two aunts, then 100% of the time such a case is one of the "true" cases as "true" is defined by being a candidate as derived in step 4. Data mining software is run for first the genetic principles and then the cancer pattern expressions in the family as defining characteristics. An arithmetic calculation is then made to determine what percent of all the "true" cases (i.e., the percent of the candidate set from step 4) meet any one rule. A rule that is met by at least 5% of all true cases, which is then defined as a significant rule, is examined, and all attributes in such significant rules are listed and are determined to be significant risk factors for the index cancer.

The attributes that are significant from the genetics principles list are the genetic principles which are pertinent to the selected index cancer and its pattern of presentation, while the cancers which are listed in the cancer-patterns significant rules are the pertinent cancers for the selected index cancer in question.

The outcome or output from step 5 is two sets of attributes which are comprised of entries from the genetic principles list and the cancers list. The aggregate of the attributes found in the rules that meet the 5% rule are defined to be the correlated genetic principles and cancer patterns which are coincident with and can characterize the selected index cancer pattern under consideration.

Step 6. Finally, data mining software is run again, marking as of interest the enumerated significant genetic principles and the significant cancer patterns from step 5 which shall characterize the "true" set in order to get a combined rule set of both genetic principles and cancer patterns, which characterizes the "true" set. The software derives a set of rules which uses the composite attributes that have been derived by this process (as per step 5), and which characterize the "true" set as defined. The set of all rules in this step 6 which are significant (i.e., 5% or more of the "true" set meet the rule) constitute the hereditary cancer rules which recognize the hereditary cancer pattern for the index cancer selected. Thus the set of all such rules in this stage is the hereditary cancer recognizer for the index cancer originally picked. The cancer attributes which arise in step 6 in the final set constitute the final output set of associated cancer attributes and are determined to be the highest correlated cancers for the index cancer. These associated cancers, determined to be the highest correlated cancers, are the cancers used to instantiate any rule.

Step 7. For any single new cancer family history, if the history can meet any one of the defining rules from the final output of step 6, this cancer family history is determined to exhibit a hereditary pattern.

These above seven steps create defining patterns which characterize the index cancer at issue. This process is independent of any diagnostic hereditary cancer history labeling or assignment. It is automatic in that following the process leads to a rule set if one exists.

The following implementation was conducted:

1. The master file from HCI was combined, unified, and made compatible with the theoretic approach proposed, with all identifiers removed to preserve total confidentiality as shown in Example 1.

2. A dBase program was used that permits us to select cancer type(s) t from the master file and permute records through transposition of genetic histories as shown in Example 2.

3. Core principles were defined which assign a numerical ranking to every case, ranking the case (with value v) in terms of its candidacy for hereditary status as shown in Example 3.

4. A dBase program was used that applies the set of principles in order to define a set of hereditary candidates and then delivers these to our data mining software. Then, as shown in Example 4, data mining software was used to determine clinical rules which further characterize the interesting candidate cases by their family pattern of cancer.

5. Experiments have been run with values v for cancer type t in concert with the data mining program and have created a class of recognizers as shown in Examples 5–11.

6. Experiments and refinements of the process as well as evaluating the recognizers for usefulness have been conducted as shown in Examples 12–17.

For example, focusing on colon cancer, one process of the present invention yields a set of rules (a recognizer) so that 100% of all the cases in the independent files available to the experimenters, labeled hereditary to date by medical experts are correctly labeled by the recognizer.

We determined the nature and extent of the hereditary colon cancer cases which are not recognized, if any, in further experimentation and how to adjust the process so that the automatically constructed recognizer has greater selectivity and sensitivity. We have also replicated this effort to analogous recognizers for breast cancer, malignant melanoma, and pancreatic cancer.

EXAMPLES

The following examples are provided to further illustrate the present invention and are not intended to limit the invention beyond the limitations set forth in the appended claims.

Example 1

Developing a Database

A database of clinical cases was converted into an information source that permits the development of appropriate rules. The database was obtained from the Hereditary Cancer Institute (HCI) of the Creighton University School of Medicine, Omaha, Nebr. This database had cases describing patient cancer family data. There was not an independent assessment in the database which validated that a patient in the database is in fact a hereditary-cancer-affected person. The database represented people who contacted HCI, and so we believed there were some hereditary families in the database. However this database did not have a hereditary cancer assignment of "true" or "false" regarding each case (in which true=a hereditary cancer carrier), although such an assignment is needed for either traditional neural network or data mining methodology.

Example 2

Expanding an Initial Database into Varied Patterns

The HCI database was modified to multiply our case patterns as much as possible. This process is described below:

Let R be all records in the currently available HCI database of cancer patients. There were about 56,000 such cases, comprised of sporadic cases, hereditary, familial, putative, and unknown designation of 45 different types of cancer, although we do not know per individual which designation applies. First these records are split into two separate cases, one "record" being the patient with the information describing his or her maternal side, and another record describing the paternal side. This split makes analysis much easier, and results in two genetically separate patterns to consider for each original client in the database. This new database of approximately 100,000 patterns is R'. Second, we took R' and for every cancer case in R' we looked at the family of each patient or client, identified any cancers occurring in another family member, and wrote another record describing the cancer history from that family member's point of view. Thus the cancer-affected individuals in the family are viewed as proband themselves, with the record properly reconfigured to reflect this history. For example, if a female patient had breast cancer, and the patient's mother and daughter did also, then additional records would be added to the database from the viewpoint of the person's affected mother and daughter. First, a record would be added for the mother, indicating she had a daughter and a granddaughter with breast cancer. Then another record would be added for the daughter, indicating she had a mother and grandmother with breast cancer. If the mother had a sister with colon cancer, yet another record would be added for this sister, indicating she had colon cancer, had a sister with breast cancer, a mother with breast cancer, and a niece with breast cancer. In this way, a pattern can be expanded into the many ways the pattern might be viewed or presented. We say we "pivot" on each cancer family member, adding the alternate perspective of that member to the database. Once complete, we now have Ro, the "pivoted" database for R'. This strategy increases our theoretical pattern set to perhaps 500,000 patterns.

Example 3

Defining Genetic Principles

We presented the five basic broad-level genetic principles that may apply in any hereditary pattern, which were:

a. Inheritance may show up more than once in the same generation (horizontal or generational inheritance). This principle will be made precise as a function $f_1$ in the application example below and is abbreviated GENLINE in the computer output.

b. Inheritance may show up from the prior generation to a subsequent generation (which we call inter-generational or vertical inheritance). This principle will be made precise as a function $f_2$ in the application example below and is abbreviated VERLINE in the computer output.

c. There may be numerous instances of various (different) manifestations of the pattern over multiple generation (general intensity). This principle will be made precise as function $f_3$ in the application example below and is abbreviated INTENSITY in the computer output.

d. There may be numerous instances of the same manifestation of the pattern over multiple generations so that there is a specific intensity of some specific manifestation. This principle will be made precise as function $f_4$ in the application example below and is abbreviated SPECINTEN in the computer output.

e. Since it is genetically based, it occurs sooner (early age of onset) in the age of the organism expressing the pattern (i.e., as soon as the genes can begin expressing themselves) rather than at later ages such as patterns caused by external (i.e., non-genetic events whose probability of occurrence can build over time and thus more and more likely occur as more and more time passes (late age of onset). This principle will be made precise as a function $f_5$ in the application example below and is abbreviated EARLY in the computer printout.

We define a quantifiable assignment of values for the above set of five genetic attribute features which help distinguish a potential hereditary pattern.

We denote $\bar{x}^k$ as a single record of some person or case in the Ro, where the bar over the x indicates the x is a vector of information containing the family cancer history for relatives for each person x, and the k indicates the kth person in the total database Ro. We will define five functions ($f_i$) of $\bar{x}^k$ as follows:

$f_1(\bar{x}^k)$: Generational Cancer—this attribute states that one or more cancers on the same generational line, on the same side, is an interesting attribute. We assigned the value:

$f_1(\bar{x}^k)=1$ if there is one cancer of one type on one generational line.

$f_1(\bar{x}^k)=2$ if there are two cancers of the same type on the same line.

$f_1(\bar{x}^k)=3$ if there are three or more same cancers on the same line.

$f_2(\bar{x}^k)$: Inter-generational cancer—this attribute states that one or more cancers, on the same generational side, between generations, is an interesting attribute. We assigned:

$f_2(\bar{x}^k)=1$ if there is one cancer on one generational line.

$f_2(\bar{x}^k)=2$ if there are 2 identical cancers on 2 different generational lines.

$f_2(\bar{x}^k)=3$ if there are three or more identical cancers among generations.

$f_3(\bar{x}^k)$: Overall cancer intensity—this attribute states that a large percent of the relatives having cancers on the same side of the family (not counting children) is an interesting attribute. We assigned:

$f_3(\bar{x}^k)=1$ if up to 33% of the family on the same side had cancer.

$f_3(\bar{x}^k)=2$ if up to 66% of the family on the same side had cancer.

$f_3(\bar{x}^k)=3$ if more than 66% of the family on the same side had cancer.

$f_4(\bar{x}^k)$: Specific cancer intensity—this attribute states that a large number of identical cancers on the same side of the family is an interesting attribute. We assigned:

$f_4(\bar{x}^k)=1$ if there is more than one identical cancer on the same side.

$f_4(\bar{x}^k)=2$ if there are more than two identical cancers on the same side.

$f_4(\bar{x}^k)=3$ if there are more than 3 identical cancers on the same side.

$f_5(\bar{x}^k)$: Early age of cancer onset—this attribute states that early age of onset of cancer is an interesting attribute. We assigned:

$f_5(\bar{x}^k)=1$ for each cancer diagnosed by the age of 50.

$f_5(\bar{x}^k)=2$ for each cancer diagnosed by the age of 45

$f_5(\bar{x}^k)=3$ for each cancer diagnosed by the age of 35.

Using the five principles or functions above, we apply each function to each case record to assign points depending on the data contained in each record of the case under review. The more points, the more the case is very serious in that it is reflecting an example of a hereditary inheritance. We add the five functional values together to get a total sum (and we may multiply any one of the functions times a weight if we wish to emphasize that attribute more than another. A specific point total is selected, and for all cases of the index cancer that is selected (e.g., colon cancer proband cases) that accrue these many points or more, we label this the defining subset from the larger set which will be used to define the recognizer. This set of cases whose point total is above a threshold is the "true" set for purposes of using standard data mining algorithms to characterize the cases in the set. Formalistically, for our colon cancer recognizer, we assign the value "true" to a case x in the database if:

$$\sum_{i=1}^{5} a_i f_i(x) \geq v$$

for a threshold value v and for $a_i$ where $a_i$ is any numerical weight for $f_i$.

Example 4

As noted in Example 2, a database is obtained and the individual cases permuted so that variations in patterns are obtained. As per Example 3, each individual patient history (or case) is evaluated in terms of how it meets each of the hereditary principles (in the instant case, by a computer program). Example 3 shows how, for an instant application, numeric values are provided with an assignment strategy so that a case accrues points depending on how many cancers there are in the family, the type and extent, etc. All cases that pass a selected threshold value in Example 3 are the candidate (or "true" cases) for purposes of this invention. The database with the true cases marked as such, and the other cases marked false, is now fed into a standard data mining package (in the instant case, we use DATALOGIC-R/version 1.3 from Reduct, Inc.) Along with, for each case, the specific numeric values for each of the five hereditary principles that each case accrued. The data mining algorithm is directed to first characterize the true cases in terms of the hereditary principles. For the actual database of 56,000 cases from HCI and for all the permutations of cases as described, when focusing on colon cancer cases the following results were obtained in the copy of the computer printout below (where the symbol>=means "greater than or equal to" and the symbol <> means "strictly less than or strictly greater than"):

```
1 |    | I[EARLY>=6] & [SPECINTEN>=2] & [GENLINE>=2] & [VERLINE>=1]
  |  OR
2 |    | I[EARLY>=6] & [SPECINTEN>=3]
  |  OR
3 |    | I[INTENSITY< >1] & [EARLY>=6]
  |  OR
4 |    | I[EARLY>=9]
  |  OR
5 |    | I[EARLY>=6] & [SPECINTEN>=2] & [GENLINE>=3]
  |  OR
6 |    | I[EARLY>=6] & [GENLINE>=3] & [VERLINE>=1]
  |  OR
7 |    | I[EARLY>=6] & [VERLINE>=2]
  |  OR
8 |    | I[INTENSITY< >1] & [EARLY>=3] & [SPECINTEN>=3] & [GENLINE>=2] & [VERLINE>=1]
  |  OR
9 |    | I[INTENSITY< >1] & [SPECINTEN>=3] & [GENLINE>=2] & [VERLINE>=2]
  |  OR
10 |   | I[EARLY>=3] & [SPECINTEN>=3] & [GENLINE>=3] & [VERLINE>=2]
   |  OR
11 |   | I[INTENSITY< >1] & [EARLY>=3] & [SPECINTEN=2] & [VERLINE>=2]
```

In these 11 rules, 90.21% of all colon cancer cases among the "true" cases can be characterized. This means over 90% of all the "true" cases meet one of these 11 rules. Since there are 1,020 "true" cases, the 5% significance rule means that 5% of 1,020 or 51 cases at the minimum must meet any one rule for the rule to be counted as significant. One of many standard reports from the software gives these figures: Rule 1—686 cases; Rule 2—713 cases; Rule 3—330 cases; Rule 4—455 cases; Rule 5—720 cases; Rule 6—652 cases, Rule 7—298 cases; Rule 8—368 cases; Rule 9—207 cases; Rule 10—305 cases or Rule 11—8 cases.

Applying the 5% significance role, role 11 is omitted, and the rest remain. Inspecting the attributes (the hereditary principles) which occur in the 10 viable rules, we find all but "INTENSITY" are used. INTENSITY occurs only with a <> sign in all rules and since one of the viable choices is "strictly less than 1", the value of zero is a choice, meaning zero INTENSITY is a permissible condition (i.e., no INTENSITY). So this attribute falls away, and the remaining are significant.

This procedure is repeated using all of the cancers that occur in the family histories of all the cases. The results are again presented below from the same software package. In this run, only the twelve rules 1, 2, 3, 4, 6, 7, 8, 9, 10, 11, 13 and 14 had more than 51 cases meeting the specific rule.

| | |
|---|---|
| 1 | \|[CA14_A<1] & [4<= CA1_A <=14] & [CA1_B>=2] |
| | OR |
| 2 | \|[CA1_A>=6] & [1<= CA1_B <=7] |
| | OR |
| 3 | \|[4<= CA1_A <=14] & [1<= CA1_B <=7] & [CA2_A=1] |
| | OR |
| 4 | \|[4<= CA1_A <=14] & [CA9_B>=1] |
| | OR |
| 5 | \|[CA2_A>=1] & [CA9_B<=0 or CA9_B>=2] & [CA2_B>=1] |
| | OR |
| 6 | \|[CA14_A<1] & [4<= CA1_B <=7] |
| | OR |
| 7 | \|[2<= CA1_B <=7] & [CA2_A<=0 or CA2_A>=2] & [CA2_B>=1] |
| | OR |
| 8 | \|[4<= CA1_A <=14] & [CA2_B>=1] |
| | OR |
| 9 | \|[4<= CA1_A <=14] & [CA2_A>=2] & [CA24_A<=0 or CA24_A>=3] |
| | OR |
| 10 | \|[CA2_A>=3] |
| | OR |
| 11 | \|[CA1_A>=8] & [CA2_A>=1] |
| | OR |
| 12 | \|[CA42_A>=1] & [1<= CA1_B <=7] |
| | OR |
| 13 | \|[CA1_A<=3 or CA1_A>=8] & [CA1_B>=3] & [CA2_A<=0 or CA2_A>=2] & [CA9_B<=0 or |
| | \|CA9_B>=2] |
| | OR |
| 14 | \|[CA1_A>=6] & [CA24_A>=1] |
| | OR |
| 15 | \|[CA1_B=2] & [CA2_A>=1] & [CA9_B<=0 or CA9_B>=2] |
| | OR |
| 16 | \|[CA3_A<1] & [1<= CA1_B <=7] & [CA2_A>=1] & [CA6_B>=1] |
| | OR |
| 17 | \|[CA2_A>=2] & [CA6_B>=1] |
| | OR |
| 18 | \|[CA6_B>=1] & [CA24_A>=1] |
| | OR |
| 19 | \|[CA3_A>=1] & [4<= CA1_A <=14] & [CA2_A<=0 or CA2_A>=2] |
| | OR |
| 20 | \|[CA3_A>=1] & [CA1_A>=6] |
| | OR |
| 21 | \|[CA1_A<=3 or CA1_A>=8] & [CA2_A>=2] & [CA24_A>=1] |
| | OR |
| 22 | \|[CA1_B=2] & [CA9_B>=1] & [CA2_B<=0 or CA2_B>=3] |
| | OR |
| 23 | \|[CA3_A<1] & [CA18_A>=1] & [CA6_B>=1] |
| | OR |
| 24 | \|[4<= CA1_A <=14] & [CA2_A=1] & [CA24_A>=1] |
| | OR |
| 25 | \|[CA14_A>=1] & [CA9_B>=1] |
| | OR |
| 26 | \|[CA1_A>= 6] & [CA2_A>=1] & [CA18_A>=1] |
| | OR |
| 27 | \|[CA3_A>=1] & [1<= CA1_B <=7] & [CA2_A<=0 or CA2_A>=2] |
| | OR |
| 28 | \|[CA14_A>=1] & [CA2_B>=1] |
| | OR |
| 29 | \|[CA2_B>=3] |
| | OR |
| 30 | \|[3<= CA1_B <=7] & [CA18_A>=1] |
| | OR |
| 31 | \|[CA14_A>=1] & [10<= CA1_A <=14] |
| | OR |
| 32 | \|[CA3_A>=1] & [CA9_B>=1] |
| | OR |
| 33 | \|[CA1_B>=4] & [CA2_A>=1] |
| | OR |
| 34 | \|[CA1_A>=15] |
| | OR |
| 35 | \|[CA3_A<1] & [CA18_A>=2] & [CA24_A<=0 or CA24_A>=3] |
| | OR |
| 36 | \|[CA14_A>=1] & [4<= CA1_A <=14] & [CA2_A>=1] & [CA18_A<=0 or CA18_A>=2] |
| | OR |
| 37 | \|[CA42_A<1] & [CA14_A<1] & [CA1_A>=6] & [CA18_A>=1] |
| | OR |
| 38 | \|[CA2_A>=1] & [CA6_B>=2] |
| | OR |
| 39 | \|[CA3_A>=1] & [CA18_A<=0] & [CA16_B>=1] |
| | OR |
| 40 | \|[CA14_A>=1] & [CA18_A>=2] |

```
    |   OR
41  |     | |[4<= CA1_A <=14] & [CA24_A>=3]
    |   OR
42  |     | |[CA3_A>=1] & [CA18_A>=2] & [CA24_A>=1]
    |   OR
43  |     | |[CA18_A>=1] & [CA24_A>=3]
    |   OR
44  |     | |[CA2_B>=1] & [CA6_B>=2]
```

Looking at the specific cancers that occur in these rules, we see the following codes (and their meaning) survive the 5% rule (the designation of A or B after a code such as CA1 for colon cancer indicates a first-degree relative if there is an A—or a second-degree if there is a B):

CA1—colon cancer wish to use in classifying the "true" cases, and since we have derived in the two steps above the key elements, we are ready for the final run. The results are given below:

```
 1 |     | |[EARLY>=6] & [SPECINTEN>=3]
   |  OR
 2 |     | |[GENLINE=3] & [EARLY>=6] & [SPECINTEN>=2]
   |  OR
 3 |     | |[GENLINE=3] & [EARLY>=6] & [VERLINE>=1]
   |  OR
 4 |     | |[[EARLY>=9]
   |  OR
 5 |     | |[EARLY>=6] & [SPECINTEN>=2] & [VERLINE>=1] & [CA1_B<=0 or CA1_B>3]
   |  OR
 6 |     | |[EARLY>=6] & [VERLINE>=2]
   |  OR
 7 |     | |[GENLINE=3] & [EARLY>=3] & [SPECINTEN>=3] & [VERLINE>=2]
   |  OR
 8 |     | |[EARLY>=3] & [CA1_A>=6] & [VERLINE>=1]
   |  OR
 9 |     | |[GENLINE=3] & [EARLY>=3] & [4<= CA1_A <=9] & [VERLINE>=1] & [1<=CA1_B <=5]
   |  OR
10 |     | |GENLINE=3] [EARLY>=3] & [SPECINTEN>=3] & [CA1_A<3 or CA1_A>=8] &
   |     | |[CA2_A>=1]
   |  OR
11 |     | |[GENLINE=3] & [EARLY>=3] & [VERLINE>=2] & [1<= CA1_B <=5] & [CA2_A<=0 or
   |     | |CA2_A>=2]
   |  OR
12 |     | |[EARLY>=3] & [SPECINTEN>=3] & [CA2_A>=2]
   |  OR
13 |     | |[EARLY>=3] & [CA1_B>=2] & [CA2_A>=1]
   |  OR
14 |     | |[GENLINE=3] & [EARLY>=3] & [CA1_B=2]
   |  OR
15 |     | |[EARLY>=3] & [8<= CA1_A <=9]
   |  OR
16 |     | |[GENLINE=3] & [4<= CA1_A <=9] & [VERLINE>=2] & [CA2_A>=1]
   |  OR
17 |     | |[SPECINTEN>=3] & [CA1_A<=3] & [VERLINE>=2] & [CA1_B<=0 or CA1_B>=3] &
   |     | |[CA2_A<=0 or CA2_A>=2]
   |  OR
18 |     | |[EARLY>=3] & [CA1_B>=6]
   |  OR
19 |     | |[GENLINE< >3] & [SPECINTEN>=3] & [VERLINE<=1] & [CA2_A>=1]
   |  OR
20 |     | |GENLINE< >3] & [EARLY>=3] & [SPECINTEN>=2] & [VERLINE>=2] & CA1_B<=0 or
21 |     | |[EARLY>=3] & [SPECINTEN<=1] & [VERLINHE>=2] & [CA1_B<=0 or CA1_B>= 3] &
   |     | |[CA2_A>=1]
```

CA2—endometrial cancer
CA9—stomach cancer
CA24—ovarian cancer
CA14—pancreatic cancer These five cancers in the rules above characterize nearly 70% of all the cases. Since we now have characterized the significant principles and significant cancers that can classify the "true" cases, we run the data mining software one more time marking just these principles and cancers to be used in combination as the elements of the permissible rules. Data mining algorithms let you specify what attributes you We again apply the 5% rule to get the final, significant rule set. All rules taken together characterize more than 93% of all of the true cases, indicating that this rule set very strongly class&lies the true set. Looking at the cases that meet each rule, the first 16 rules meet the 5% cutoff, and the remaining do not. Inspection of the cancers which occur in these 16 rules yields just two: CA1 and CA2 (colon and endometrial cancer). Since this is the colon cancer recognizer, it is a tautology that added colon cancers will define a hereditary condition. Thus the next, non-colon cancer occurring, endometrial cancer, is identified as the most highly correlated cancer to colon cancer, according to this process (a true fact). To give a single interpretation of a rule, consider rule 8. Rule 8 states that IF there are at least 6 or more first degree colon cancers in the family history (CA1_A>=6) AND there are at least two different generations having either a colon or endometrial cancer (VERLINE>=1) AND at least 3 points accrue from the hereditary principle of an early age of onset (e.g., either 3 cases under 50, or 1 under 50 and 1 under 45, or 1 under 35, etc), THEN this rule is met by such a case history and the case pattern is one of hereditary colon cancer.

Example 5

Hereditary Breast Cancer Recognizer Results

An automated recognizer has been created for hereditary breast cancer. The essence of the hereditary breast cancer recognizer is that the recognizer hypothesizes that the fundamental "issues" in hereditary breast cancer are comprised of:

breast, breast—ovarian, breast—endometrial;

breast—prostate, and breast—colon cancer patterns.

When just the maternal side was considered, interestingly, there was a somewhat different recognizer defined than when the paternal side was considered. Specific rules with minimum number of cases are given by the defined (maternal side only) recognizer, involving (1st degree breast cancer)

(1st degree breast)+(2nd degree breast cancer)

(1st degree breast)+1st or 2nd degree prostate)

(1st or 2nd degree breast)+(1st degree ovarian)+(1st or 2nd degree colon)

(1st degree breast)+(2nd degree breast)+(1st or 2nd degree colon)

These rules are totally numerically precise e.g., one numerically allowed pattern of "early age presentations" requires either one breast cancer before the age of 35 with another before the age of 45; another acceptable "early age presentation" would be two before the age of 45 and one before the age of 50. It is also important to observe that each rule derived is in effect a family of rules with a wide number of variations which are precisely specified for different values of variables in each rule.

Example 6

Predicted Syndromes

Associated syndromes for each cancer type t are summarized below. For each cancer type t, the associated cancers that are significant in support of a hereditary pattern are listed in Table 2.

TABLE 2

| Colon | Melanoma | Pancreatic |
| --- | --- | --- |
| endometrial/uterine | small intestine | ovarian |
| kidney | cervix | stomach |
| stomach | lung | brain |
| pancreas | stomach | lung |
| lung | lip | tongue |
| ovarian | urinary bladder | prostate |
|  | pancreatic | lip |

TABLE 2-continued

| Breast-maternal | Breast-paternal | Ovarian |
| --- | --- | --- |
| ovarian | ovarian | breast |
| colon | prostate | endometrial/uterine |
| prostate | endometrial/uterine | colon |
| endometrial/uterine | colon | lung |
|  | lung | prostate |
|  | stomach |  |

The most highly correlated cancers for various cancer types are summarized below in Table 3.

TABLE 3

| Cancer Type | Key Correlated Cancer |
| --- | --- |
| colon | endometrial |
| breast-maternal | ovarian |
| breast-paternal | ovarian |
| ovarian | breast |
| pancreatic | ovarian |
| melanoma | small intestine |

Although a single key associated cancer can be easily linked to each cancer type, the other cancers that support or reinforce a type suggest a syndrome nonetheless. For example, the results predict the following combinations for ovarian and breast cancer as shown in Table 4:

TABLE 4

| Ovarian Syndromes | Breast Syndromes (maternal side only) |
| --- | --- |
| ovarian-breast | breast-ovarian |
| ovarian-endometrial | breast-endometrial |
| ovarian-colon | breast-colon |
| ovarian-prostate | breast-prostate |
| ovarian-lung |  |

Example 7

Ovarian Cancer Pattern Rules

A person with ovarian cancer has a hereditary cancer pattern if there are additionally at least the following:

Two or more 2nd-degree ovarian cancer cases
or
One 1st-degree ovarian & two 1st-degree breast cancer cases
or
Two 1st-degree breast & One 1st-degree endometrial cancer Example 8

Breast—Maternal Side

A person with breast cancer has a hereditary cancer pattern if there are additionally at least the following:

Two 1st-degree breast cancers & two 2nd-degree breast cancers (all on the maternal side)
Or
Two 1st-degree breast cancers & one 2nd-degree breast and one 2nd-degree colon cancer (all on the maternal side)
Or One 1st-degree breast cancers & one 2nd-degree prostate cancer
(all on the maternal side)

Example 9

Breast—Paternal Side

A person with breast cancer has a hereditary cancer pattern if there are additionally at least the following:

Three 1st-degree breast cancers & one 2nd-degree breast cancer
(all on the paternal side)
Or
Two 1st-degree breast cancers & one 2nd-degree ovarian cancer
(all on the maternal side)

Example 10

Pancreatic Cancer

A person with pancreatic cancer has a hereditary cancer pattern if there are additionally at least the following:

Two 1st-degree pancreatic cancers & two 2nd-degree pancreatic cancers
or
Three 1st-degree pancreatic cancers & one (either 1st-degree tongue or 1st-degree melanoma)
Or
Two 1st-degree brain cancers
or
One 2nd-degree stomach cancer

Example 11

Melanoma

A person with melanoma has a hereditary cancer pattern if there are additionally at least the following:

Two 1st-degree melanoma & one 1st-degree lung cancer
or
Four 1st-degree melanomas
or
One 1st-degree melanoma & one 2nd-degree urinary bladder cancer
or
One 1st-degree small intestine cancer
or
Two 1st-degree cervical cancer
or
One 2nd-degree stomach cancer & one 2nd-degree urinary bladder cancer
or
One 1st-degree lung cancer & one 1st-degree lip cancer
or
Two 1st-degree lip cancers
or
One 1st-degree stomach cancer & one 1st-degree lip cancer
or
One 1st-degree cervical cancer & one 2nd-degree stomach cancer

Example 12

Validation Procedures

Once a recognizer was constructed, the recognizer was validated. These steps included: 1) review the rules and compare then with any prior rule sets derived by expert knowledge engineering (such as a derived a rule set developed from an expert, such as Dr. Henry T. Lynch); 2) inspect all new cancer family history cases that are consistent with this rule set to determine whether in fact hereditary cancer cases, as diagnosed by experts, are being distinguished from non-cases by the invention; and 3) determine which cases are possibly included which are not hereditary and vice versa (type I and type II errors) and adjust the entire process if need be to improve the outcome.

The process of automated recognizer rule set construction was assessed and validated with a priori knowledge which was available for hereditary colon cancer. Similarly the validation for breast cancer, melanoma, and ovarian cancer was repeated. Through this assessment process, the automated recognizer development process was refined and was shown to produce a powerful recognizer development technique. Further validation was achieved by running the recognizer against prior cancer cases for which we had Dr. H. T. Lynch's diagnosis regarding their hereditary nature.

This entire design process was also generalized by positing a universe of genetic principles for all the cases of cancer, and then letting the rule hypothesis component posit rules (i.e., a selection from the genetic principles) which characterize cases of hereditary cancer. For example, for every cancer case, the race, hair color, and so forth along with the age of onset, the number of cancers, and other possible genetic principles were itemized. Then using the exact same process, the rules classify the hereditary cancer cases by pertinent genetic principles such as "cancer patients tend to be younger," "have more instances in their family," and so forth. Thus the pertinent genetic principles from among all principles which could be speculated are identified using the same process as presented above.

Example 13

Study Evaluating Significant Factor Identification

This study compared the responses of Dr. Henry T. Lynch and Dr. Stephen J. Lemon of HCI to a set of factors isolated by the Recognizer in its analysis of hereditary colorectal cancer (HCRC) cases. This set of outcomes corresponds to key factors the Recognizer identifies as possibly relevant to incorporate into its decision-making logic to recognize HCRC. These factors are defined by the Recognizer as useful in its efforts to construct a set of rules to define HCRC.

A list of 42 cancers was provided to Dr. Lynch and Dr. Lemon, and each was asked separately to mark a ranking using the scale for each cancer as shown in Table 5. The list of cancers was taken from the list which encoded the database used to create the Recognizer. No Recognizer results were supplied to either physician ahead of time, and no collaboration between the two physicians occurred in selecting a ranking.

TABLE 5

Rankings Indicating Extent To Which Each
Cancer Reinforces Or Help Confirms A
Hereditary Colon Cancer Syndrome:

1 = Definitely - solid data to support relationship
2 = Probably - growing evidence of relationship
3 = Possibly - speculative relationship at this time
4 = Not Relevant - no known relationship In comparing the results of the Recognizer system's selections of most likely HCRC-associated cancers with the physicians' ranking, the following results were obtained in Table 6.

TABLE 6

| HCRC-related cancers listed by any responder | Recognizer Ranking | Dr. Lynch's Ranking | Dr. Lemon's Ranking |
|---|---|---|---|
| Endometrial/Uterine | Definitely | Definitely | Definitely |
| Kidney/Ureter/Renal Pelvis | Definitely | Definitely | Definitely |
| Stomcah | Definitely | Definitely | Definitely |
| Small Intestine | Definitely | Definitely | Definitely |
| Pancreas | Definitely | Definitely | Definitely |
| Ovarian | Definitely | Definitely | Probably |
| Liver/Intrahepatic | Not Relevant | Definitely | Definitely |
| Cervix | Definitely | Not Relevant | Probably |
| Lymph Nodes | Not Relevant | Not Relevant | Definitely |
| Appendix | Not Relevant | Not Relevant | Definitely |
| Gallbladder/Bile Duct/Ampulla of Vater | Not Relevant | Possibly | Definitely |

The Recognizer discovered six of seven (86%) of the "definitely related" cancers which Dr. Lynch identified, and it added one (cervix) that Dr. Lynch did not identify. With respect to Dr. Lemon, the Recognizer discovered 5 "definitely related" cancers of the nine which Dr. Lemon identified (56%), and disagreed on four others (lymph nodes, liver/intrahepatic, gallbladder/bile duct/ampulla of Vater, and appendix). The Recognizer and Dr. Lemon were also in close agreement on two other choices ("definitely" versus "probably" on ovarian and cervix). Hepatobiliary cancer did not specifically appear in the database as a coded choice, although Dr. Lynch and Dr. Lemon both had wished to include it as another choice. The Recognizer did not select either Hepatobiliary-related entry which was available to it (liver/intrahepatic or gallbladder/bile duct/ampulla of Vater) although each was selected by either Dr. Lynch or Dr. Lemon."

The Recognizer was in accord in six of seven cases (86%) on HCRC-related cancers for which Drs. Lynch and Lemon were in accord (ranking of 1 or 2). The system essentially considered 35 cancers as irrelevant, and of these, Drs. Lynch and Lemon were in mutual concurrence, ranking each 3 or 4, for 29 of them (81%). If one considers the frequency of occurrence of the associated cancers for the cancers correctly identified by the Recognizer, (i.e., those for which there was agreement between Dr. Lynch and Dr. Lemon), the Recognizer defined critical attributes for its focus most of the time.

There is a second use of such results by the Recognizer over and above automated HCRC detection. There is clinically diagnostic value in the discovery of associated cancers which help confirm a hereditary pattern. In addition, the identification of associated cancers helps guide future gene discovery efforts, as well as assists in the proper interpretation of gene-testing results.

This first stage evaluation of initial factors selected by the Recognizer suggested that use of such Recognizers is applicable over a wide sampling of typical cases with a very high level of sensitivity in its recognition capability.

Example 14

An Evaluation of Patterns

The purpose of this study was to ascertain how well the Recognizer created valid patterns of HCRC which it uses to evaluate a case.

Drs. Lynch and Lemon were asked to indicate agreement or disagreement with a list of 16 clinical patterns to the extent that each pattern would permit the designation of HCRC for an individual presenting with such a pattern. Each gave an independent assessment, and each did not know the response of the Recognizer.

The patterns were created by the Recognizer using (a) its convergence to a final list of critical factors in concert with (b) its final output of clinical rules which combine these factors into patterns it uses to characterize HCRC. The results of the sixteen patterns presented for evaluation are given in Table 7 and the sixteen patterns are listed in Table 8.

TABLE 7

| Would the Following Pattern permit the Conclusion of HCRC? | Dr. Lynch's Response | Dr. Lemon's Response |
|---|---|---|
| #1 | Yes | Yes |
| #2 | Yes | Yes |
| #3 | Yes | Yes |
| #4 | Yes | Yes |
| #5 | Yes | Yes |
| #6 | Yes | Yes |
| #7 | Yes | Yes |
| #8 | Yes | Yes |
| #9 | Yes | Yes |
| #10 | Yes | Yes |
| #11 | Yes | Yes |
| #12 | Yes | Yes |
| #13 | Yes | Yes |
| #14 | Yes | Yes |
| #15 | Yes | Yes |
| #16 | Yes | Yes |

Drs. Lynch and Lemon agreed with all 16 patterns the Recognizer had created. The Recognizer's final output was highly sensitive in detecting HCRC.

Table 8

1. All on the same side of the family:
   a. the proband has colon cancer, and
   b. there are more than 3 identical cancers (either colon or endometrial), and
   c. cancer(s) (colon or endometrial) with early onset total a minimum of 6 points (where cancer by age 35=3 points; between 36–45=2 points; between 46–49=1 point)
2. All on the same side of the family:
   a. the proband has colon cancer, and
   b. there are 3 or more of the same cancer (either colon or endometrial) in the same generation, and
   c. there are 2 or more identical cancers, and
   d. cancer(s) (colon or endometrial) with early onset total a minimum of 6 points (where cancer by age 35=3 points; between 36–45=2 points; between 46–49=1 point)
3. All on the same side of the family:
   a. the proband has colon cancer, and
   b. there are 3 or more of the same cancer (either colon or endometrial) in the same generation, and
   c. cancer(s) (colon or endometrial) with early onset total a minimum of 6 points (where cancer by age 35=3 points; between 36–45=2 points; between 46–49=1 point)
4. All on the same side of the family:
   a. the proband has colon cancer, and
   b. cancer(s) (colon or endometrial) with early onset total a minimum of 9 points (where cancer by age 35=3 points; between 36–45=2 points; between 46–49=1 point)
5. All on the same side of the family:
   a. the proband has colon cancer, and b. there are 2 or more identical cancers (either colon or endometrial), and c. cancer(s) (colon or endometrial) with early onset total a minimum of 6 points (where cancer by age 35=3 points; between 36–45=2 points; between 46–49=1 point)

6. All on the same side of the family:
   a. the proband has colon cancer, and
   b. there are 2 or more identical cancers (either colon or endometrial), and
   c. there are identical cancers (either colon or endometrial) in 2 or more generations, and
   d. cancer(s) (colon or endometrial)with early onset total a minimum of 6 points (where cancer by age 35=3 points; between 36–45=2 points; between 46–49=1 point)

7. All on the same side of the family:
   a. the proband has colon cancer, and
   b. there are 3 or more of the same cancer (either colon or endometrial) in the same generation, and
   c. there are 3 or more identical cancers (either colon or endometrial) in 2 or more generations, and
   d. cancer (colon or endometrial) with early onset total a minimum of 3 points (where cancer by age 35=3 points; between 36–45=2 points; between 46–49=1 point)

8. All on the same side of the family:
   a. the proband has colon cancer, and
   b. there are 6 or more first degree colon cancers, and
   c. cancer(s) (colon or endometrial) with early onset total a minimum of 3 points (where cancer by age 35=3 points; between 36–45=2 points; between 46–49=1 point)

9. All on the same side of the family:
   a. the proband has colon cancer, and
   b. there are 3 or more of the same cancer (either colon or endometrial) in the same generation, and
   c. there are 4 or more first degree colon cancers, and
   d. there is 1 or more second degree colon cancer, and
   e. cancer(s) (colon or endometrial) with early onset total a minimum of 3 points (where cancer by age 35=3 points; between 36–45=2 points; between 46–49=1

10. All on the same side of the family:
    a. the proband has colon cancer, and
    b. there are 3 or more of the same cancer (colon or endometrial) in the same generation, and
    c. there are 3 or more first degree colon cancers, and
    d. there is 1 or more first degree endometrial cancer, and
    e. cancer(s) (colon or endometrial) with early onset total a minimum of 3 points (where cancer by age 35=3 points; between 36–45=2 points; between 46–49=1 point)

11. All on the same side of the family:
    a. the proband has colon cancer, and
    b. there are 3 or more of the same cancer (colon or endometrial) in the same generation, and
    c. there are identical cancers (colon or endometrial) in 2 or more generations, and
    d. there is 1 or more second degree colon cancer, and
    e. cancer(s) (colon or endometrial) with early onset total a minimum of 3 points (where cancer by age 35=3 points; between 36–45=2 points; between 46–49=1 point)

12. All on the same side of the family:
    a. the proband has colon cancer, and
    b. there are more than 3 identical cancers (colon or endometrial), and
    c. there are 2 or more first degree endometrial cancers, and
    d. cancer(s) (colon or endometrial) with early onset total a minimum of 3 points (where cancer by age 35=3 points; between 36–45=2 points; between 46–49=1 point)

13. All on the same side of the family:
    a. the proband has colon cancer, and
    b. there are 2 or more second degree colon cancers, and
    c. there is 1 or more first degree endometrial cancer, and
    d. cancer (colon or endometrial) with early onset total a minimum of 3 points (where cancer by age 35=3 points; between 36–45=2 points; between 46–49=1 point)

14. All on the same side of the family:
    a. the proband has colon cancer, and
    b. there are 3 or more of the same cancer (colon or endometrial) in the same generation, and
    c. there are 2 second degree colon cancers, and
    d. cancer(s) (colon or endometrial) with early onset total a minimum of 3 points (where cancer by age 35=3 points; between 36–45=2 points; between 46–49=1 point)

15. All on the same side of the family:
    a. the proband has colon cancer, and
    b. there are 8 or more first degree colon cancers, and
    c. cancer(s) (colon or endometrial)with early onset total a minimum of 3 points (where cancer by age 35=3 points; between 36–45=2 points; between 46–49=1 point)

16. All on the same side of the family:
    a. the proband has colon cancer, and
    b. there are 3 or more of the same cancer (colon or endometrial) in the same generation, and
    c. there are identical cancers in 2 or more generations, and
    d. there are 4 or more first degree colon cancers, and
    e. there is 1 or more first degree endometrial cancer Example 15

Study Evaluating Recognizer Accuracy

This study extended the focus on the specificity of the Recognizer using those cases which have arisen at several cancer centers which obtain consultation from HCI through an analysis service supported by the Institute. In the past five years, three cases representing definite HCRC patterns and four cases with putative hereditary colorectal cancer patterns have been received, per an analysis of these cases by Dr. Henry Lynch. The goal of the study was to match the already-analyzed cases to the defining patterns created by the Recognizer to see its response compared to Dr. Lynch.

Each case was matched against one or more patterns to determine if it would meet any pattern set. All patterns sets matched by each case were identified. If the case fit none of the patterns created by the Recognizer, minimum additional requirements to match at least one pattern were summarized. The results are shown in Tables 9 and 10.

TABLE 9

Colon Cancer Cases

| Case Number | Determination by Dr. Lynch | Confirmation by Recognizer | Recognizer Pattern Match | Additional Findings to Match One Pattern |
|---|---|---|---|---|
| 1 | Definite Hereditary Pattern | Yes | 1, 2, 3, 4, 5, 6, 7 | N/A |
| 2 | Definite Hereditary Pattern | Yes | 5, 6 | N/A |
| 3 | Definite Hereditary Pattern | Yes | 1, 4, 5, 6 | N/A |

TABLE 10

Colon Cancer Cases

| Case Number | Determination by Dr. Lynch | Confirmation by Recoognizer | Recognizer Pattern Match | Additional Findings to Match One Pattern |
|---|---|---|---|---|
| 1 | Putative Hereditary Pattern | No | None | Additional early onset less than age 35 to meet #5 |
| 2 | Putative Hereditary Pattern | No | None | change of ovarian cancer diagnosis to endometrial with age of onset 2 years earlier to meet #13 |
| 3 | Putative Hereditary Pattern | No | None | One additional colon cancer in same generation to meet #7 |
| 4 | Putative Hereditary Pattern | No | None | Age of onset of one of the colon cancers prior to age 35 to meet #7 and #11 |

All the definite patterns of HCRC (N=3) matched one or more of the Recognizer patterns. None of the four putative HCRC cases matched a Recognizer pattern. However the missing data elements required to match at least one pattern were minimal.

Therefore, the Recognizer gives the correct response for all definite HCRC cases, and gives a negative response in all 4 putative HCRC cases. Thus the Recognizer developed was both sensitive and specific for definite HCRC patterns.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

Example 16

Defining a Significant Rule

The construction of the rule set has in practice two components, the development of the first set of rules that use the "genetic principles" $f_{(t)}$ as defined above, and then a second component that defines cancer-presenting patterns among the cases that are contained in the candidate set (i.e., $P_t^v$).

We constructed an assignment of weights to the rules themselves in order to define which we finally included in the recognizer created for a specific $P_t^v$.

To accomplish the goal of defining significant rules, we defined the significance function $T(x)$:

$$T(x) = \left[ \frac{1 - 10x}{10} \right]$$

For any rule, let C be the number of candidate cases (i.e., $\bar{x}^k$) which meet that rule and let $C_i$ be the total number of rules in $P_t^v$ for v and t. Then a rule is significant if $$T\left( \frac{C_i}{C} \right) \leq .05$$

In effect, rules are significant if at least 5% of the cases being considered (i.e., in $P_t^v$) support or demonstrate the rule.

Example 17

Details of the Methodology: Neural Net Limitations

For completeness, we shall identify some limitations of neural net methodology as a pattern recognizer, to clarify the challenge before us. Neural nets represent complex functions which assign a certain amount of value for a particular attribute of what is being recognized. Thus the color "red" for a rose gives the flower some numerical points; "having thorns" would also; having any kind of fruit growing would be a negative indicator. By a weighted summing of the positive attributes presented and subtracting the negative, a value is obtained, which if greater than a fixed amount, indicates we have a rose. This methodology requires having possible rose attributes determined and the truth value of the assignment for "rose" (or not) given to the system so that it can balance all its weights to signal a rose. In our situation the detailed attribute universe is not known, in general, and more importantly there is no "labeling" of what constitutes a valid rose. Thus neural net methodology is not applicable to the tasks undertaken.

Another limitation is that the result of the application of neural net methodology is a strictly performance-based network, in the form of essentially a mathematical model that predicts set membership. Such networks do not lend themselves to intellectual clinical model validation although the network's performance can be measured by testing. Physicians want to know why a claim is made, not just a numerical calculation that it should be made.

What is claimed is:

1. A method for determining the existence of a hereditary disease risk in a patient, comprising the steps of:

assembling a computer a database made up of a plurality of records each pertaining to an individual and containing a history of at least one specific disease in a family of that individual, said history including a plurality of parameters relating to each family member identified in said history;

defining a plurality of functions each pertaining to said parameters and assigning predetermined weights to said functions based on values of said parameters;

for each record in said database, summing the weights obtained for each of said functions to obtain a total value for each of said functions, identifying said record as presenting a hereditary pattern if the total value is above a predetermined threshold, and grouping said identified record into a subset of records;

for each record in said database, applying expert knowledge generated rules to independently identify records as presenting hereditary patterns;

comparing said independently identified records with said subset of records, and validating defined functions if a predetermined minimum percentage of records in said subset are consistent with said independently identified records; and using and displaying said validated functions as a recognizer of hereditary disease patterns in a family history of said patient.

2. A method according to claim 1, wherein said plurality of records contain histories of instances of cancer.

3. A method according to claim 2, wherein said instances of cancer include breast, ovarian, endometrial, prostate, malignant melanoma and colon cancer.

4. A method according to claim 3, further including the step of assigning weights to particular attributes used in said functions, and defining attributes as significant in the definition of specific hereditary disease patterns if a minimum percentage of records in said subset are consistent with said independently identified records.

5. A method according to claim 1, further comprising creating an additional record in said database for each relative of said individual who is identified as having had said disease.

* * * * *